US006861087B2

(12) United States Patent
Han et al.

(10) Patent No.: US 6,861,087 B2
(45) Date of Patent: Mar. 1, 2005

(54) PREPARATION METHOD OF BIODEGRADABLE POROUS POLYMER SCAFFOLDS HAVING AN IMPROVED CELL COMPATIBILITY FOR TISSUE ENGINEERING

(75) Inventors: Dong Keun Han, Seoul (KR); Kwang Duk Ahn, Seoul (KR); Young Min Ju, Seoul (KR); Saeyoung Ahn, Seoul (KR)

(73) Assignees: Korea Institute of Science and Technology, Seoul (KR); Solco Biomedical Co., Ltd., Gyeonngi-do (KR)

( * ) Notice: Subject to any disclaimer, the term of this patent is extended or adjusted under 35 U.S.C. 154(b) by 67 days.

(21) Appl. No.: 10/270,737

(22) Filed: Oct. 16, 2002

(65) Prior Publication Data

US 2004/0043135 A1 Mar. 4, 2004

(30) Foreign Application Priority Data

Aug. 28, 2002 (KR) ........................................ 2002-51238

(51) Int. Cl.[7] ................................................ B05D 3/00
(52) U.S. Cl. ...................... 427/2.1; 427/2.24; 427/2.31; 427/491; 427/533; 427/569; 427/296
(58) Field of Search ................................. 427/2.1, 2.24, 427/2.31, 487, 488, 491, 534–536, 569, 294, 296, 307

(56) References Cited

U.S. PATENT DOCUMENTS

| 6,623,749 B2 | * | 9/2003 | Williams et al. ............ 424/423 |
| 2003/0165613 A1 | * | 9/2003 | Chappa et al. ............. 427/2.24 |
| 2003/0198968 A1 | * | 10/2003 | Matson .......................... 435/6 |

* cited by examiner

Primary Examiner—Bret Chen
(74) Attorney, Agent, or Firm—Morrison & Foerster LLP

(57) ABSTRACT

A method for modifying surface of biodegradable porous polymer scaffold for tissue engineering using a low temperature plasma discharge apparatus, and particularly, a method for inducing the biodegradable porous polymer scaffold to be hydrophilic by graft polymerizing a hydrophilic monomer on the surface of the biodegradable porous polymer scaffold, which is made of polylactic acid, polyglycolic acid or poly(lactic acid-glycolic acid) copolymer, using a low temperature plasma. The surface-modified porous polymer scaffold according to the present invention has an enhanced cell compatibility in cell culture in vitro, and promote tissue growth when the cell is transplanted into a body.

12 Claims, 1 Drawing Sheet

PREPARATION METHOD OF BIODEGRADABLE POROUS POLYMER SCAFFOLDS HAVING AN IMPROVED CELL COMPATIBILITY FOR TISSUE ENGINEERING

BACKGROUND OF THE INVENTION

1. Field of the Invention

The present invention relates to a method for modifying a surface of biodegradable porous polymer scaffold for tissue engineering using a low temperature plasma discharge apparatus.

2. Description of the Background Art

A biodegradable polymer such as polylactic acid (PLA), polyglycolic acid (PGA) or poly(lactic acid-glycolic acid) copolymer (PLGA) used as a material of scaffold for tissue engineering has been applied in various medical fields such as bone plates of screw, plate or pin shape, surgical sutures or a matrix for drug delivery, due to the characteristics such as superior degradability and mechanical property in vivo, easiness in controlling degrading rate, and easiness in forming pores.

However, the above materials are all hydrophobic, and therefore, cell compatibility and tissue compatibility are low when a tissue cell is cultured in a porous polymer scaffold, or when the polymer scaffold in which the cell is cultured is transplanted into a body. In order to solve the above problems, researches into modifying the surface of the polymer scaffold have been proceeded in various ways.

There are methods for improving the hydrophilicity and tissue compatibility such as a method of treating with an aqueous acid solution (G. Khang, S. J. Lee, J. H. Jeon, J. H. Lee and H. B. Lee, Polymer (Korea), 24, 6, 869, 2000), a method of treating with an aqueous alkali solution such as sodium hydroxide (J. Gao, L. Niklason and R. Langer), and a method of fabricating a scaffold in a hybrid form of collagen which is one of extracellular matrix components and PLA or PLGA.

However, in the conventional methods, when the aqueous acid or alkali solution is used, the scaffold itself is degraded by the aqueous acid or alkali solution to lower the mechanical properties of the scaffold, and when the collagen is used, problems of immune reaction may be caused by the use of the one of different species.

SUMMARY OF THE INVENTION

Therefore, an object of the present invention is to provide a biodegradable porous polymer scaffold which is capable of solving problems such as lack of compatibility with a cell and a tissue due to hydrophobicity of the conventional biodegradable polymer scaffold, and to a fabrication method thereof.

Another object of the present invention is to provide a method for modifying a surface of biodegradable porous polymer scaffolds for tissue engineering which is capable of solving problems such as lowering mechanical properties of polymer scaffold modified by the conventional art and problems of immune reaction caused by using an extracellular matrix of a different species.

To achieve these and other advantages and in accordance with the purpose of the present invention, as embodied and broadly described herein, there is provided a method comprising a fabrication of a porous polymer scaffold including steps of preparing a polymer scaffold sample using a polymer solution containing a biodegradable polymer and an effervescent mixture, foaming the polymer scaffold sample in an effervescent medium which is a solvent mixture of an alcohol and water, and drying the resultant, and the surface modification of the obtained polymer scaffold by making the polymer scaffold be hydrophilic through a graft-polymerization of a hydrophilic monomer on the surface of the polymer scaffold with a low temperature plasma discharge apparatus.

The foregoing and other objects, features, aspects and advantages of the present invention will become more apparent from the following detailed description of the present invention when taken in conjunction with the accompanying drawings.

BRIEF DESCRIPTION OF THE DRAWINGS

The accompanying drawing, which is included to provide a further understanding of the invention and is incorporated in and constitutes a part of this specification, illustrates embodiments of the invention and together with the description serve to explain the principles of the invention.

In the drawing.

DETAILED DESCRIPTION OF THE PREFERRED EMBODIMENTS

Figure 1:
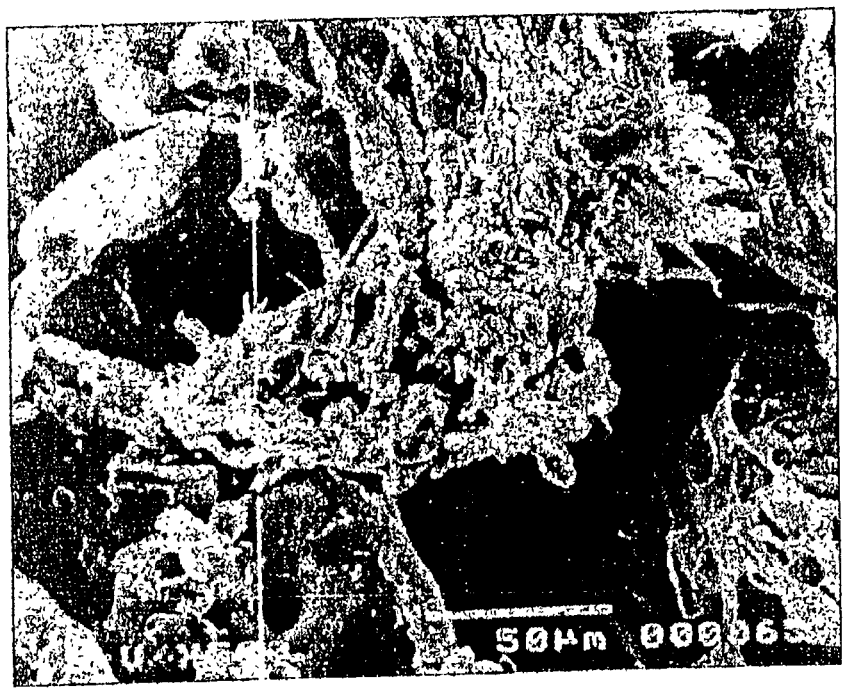
FIG. 1 is a photograph of scanning electron microscopy showing a cell growth in a polymer scaffold made of poly-L-lactic acid.

The method for fabricating a biodegradable polymer scaffold for tissue engineering having an improved cell compatibility according to the present invention comprises a) a process of fabricating a biodegradable porous polymer scaffold, and b) a process of surface modification of the biodegradable porous polymer scaffold obtained in step a) through a graft-polymerization of a hydrophilic monomer thereon with a low temperature plasma discharge apparatus.

The above process a) comprises steps of pouring a polymer solution containing a biodegradable polymer and an effervescent mixture into a frame or mold made of a polymeric material, preparing a polymer sample in a disc shape by evaporating the solvent, foaming the disc shape polymer sample in an effervescent medium which is a solvent mixture of alcohol and water, washing the sample with super-pure water and drying the sample. The above process b) comprises a graft-polymerization of an unsaturated aliphatic hydrocarbon monomer having a hydrophilic group onto a surface of the porous polymer scaffold prepared in the above process a).

Reference will be now made in detail to the preferred embodiments of the present invention, examples of which are illustrated in the accompanying drawings.

1) Fabrication of a Biodegradable Porous Polymer Scaffold

A biodegradable porous polymer scaffold is fabricated by a method which a salt leaching method and a gas foaming method are combined. That is, a biodegradable polymer is dissolved in an appropriate solvent, an effervescent mixture for forming pores is added therein, and the obtained mixture is mixed uniformly. The resulting mixture is then poured into a frame or a mold made of a silicone material having a desired shape, and then the solvent is evaporated by a freeze drying method, thereby to obtain a polymer sample in a disc shape. Subsequently, the polymer sample of disc shape undergoes a foaming process.

The biodegradable polymer used as a material of the polymer scaffold in the present invention is not limited if it is nontoxic degradable polymer in vivo. Examples include PGA, PLA (PLLA, PDLLA, and PDLA), PLGA, poly-ε-caprolactone (PCL), poly(glycolic acid-caprolactone) copolymer (PGCL), poly aminoacid, polyanhydride, polyorthoester, and copolymers and mixtures thereof. It is preferable to use PLA, PGA, PCL, PLGA, PGCL or mixtures thereof which are accepted by Food and Drug Administration (FDA) and have been used as a biodegradable polymer which can be used in a human body. Molecular weight of the biodegradable polymer is in the range of 5,000–2,000,000, and preferably, 10,000–700,000. However, it is not limited thereto.

Concentration of the polymer solution used to fabricate the porous polymer scaffold is 5–20% by weight, and chloroform, dichloromethane, acetone, dioxane, tetrahydrofuran, trifluoroethane or mixtures thereof can be used as a solvent.

The effervescent mixture used for forming pores in the present invention is a mixture of a carbonate and an organic acid. The effervescent mixture is a substance which is harmless to human body and can be used in a general medicine, and a solid which has a constant particle size and can be dissolved in water easily. Examples of the carbonate used in the present invention include sodium bicarbonate, sodium carbonate, ammonium bicarbonate, ammonium carbonate, potassium bicarbonate, calcium carbonate and mixtures thereof. However, it is not limited thereto if it is a carbonate which can generate carbon dioxide. Examples of the organic acid include citric acid, tartaric acid, succinic acid, maleic acid, fumaric acid, malonic acid, malic acid, gluconic acid, muccinic acid, partial amino acid and mixtures thereof.

The particle size of the effervescent mixture can be varied according to purpose, and generally it is suitable that the size is 5–500 μm. In the effervescent mixture, it is preferred that the carbonate:organic acid is 1:1–3:1 in a molar ratio. When two or more organic acids are used, the molar ratio between the organic acid and the carbonate is dependent on the number of carboxyl groups contained in the organic acid.

In fabricating the porous polymer scaffold, it is suitable that the amount of the effervescent mixture used such that the ratio of the effervescent mixture/polymer is 5/1–20/1 by weight.

After removing the organic solvent from the polymer sample, it is foamed. At that time, it is preferable that the foaming is performed in an effervescent medium which is an aqueous alcoholic solution containing an alcohol and water. It is for making the foaming effective by inducing the hydrophobic polymer scaffold to be settled down in the effervescent medium. Examples of alcohol which can be used for the above purpose include ethanol, methanol, isopropanol, etc. The content of the alcohol in the aqueous alcoholic solution is 1–95% by volume.

The foamed polymer sample is then washed with ultra-pure water, and then freeze-dried, thereby to obtain a porous polymer scaffold.

2) Surface Modification of the Porous Polymer Scaffold

The surface of the porous polymer scaffold is modified through a graft-polymerization of a hydrophilic monomer onto the surface of the porous polymer scaffold obtained as described above with a low temperature plasma discharge apparatus.

The process for modifying the surface of the polymer scaffold with a low plasma discharge apparatus according to the present invention can be divided into two steps. The first step is to carry out a graft-polymerization by injecting an unsaturated aliphatic hydrocarbon monomer having a hydrophilic group in a gas phase into a chamber in which the polymer scaffold is located, and after maintaining a pressure in the chamber at a constant value, performing a graft polymerization of an unsaturated aliphatic hydrocarbon monomer on the surface of the polymer scaffold by applying a radio frequency (RF) power and pulse type negative voltage in order to generate a plasma. It is preferred that the pressure when the unsaturated aliphatic hydrocarbon monomer is injected is in the range of $5 \times 10^{-2}$–$3 \times 10^{-1}$ torr, the magnitude of RF power is 50–1,000 W, and the time period to discharge the plasma is 10–300 seconds. The second step is to activate the surface of the polymer scaffold by treating the surface of the graft polymerized material with a plasma after injecting a surface activating gas such as oxygen or argon.

Examples of the unsaturated aliphatic hydrocarbon monomer having a hydrophilic group used in the present invention include acrylic acid, acrylamide, hydroxyethyl methacrylate, allyl alcohol, polyethylene glycol monoacrylate, polyethylene glycol monomethacrylate, glycidyl methacrylate, aminopropyl methacrylamide, etc. It is preferred that the polyethylene glycol monoacrylate and polyethylene glycol monomethacrylate have a molecular weight of 200–2,000, respectively.

Examples of the gases which can be used in the activating step of the surface of scaffold after the graft polymerization include oxygen, nitrogen, carbon monoxide, carbon dioxide, ammonia or mixtures thereof.

The steps of the graft polymerization of the unsaturated aliphatic hydrocarbon monomer on the surface of the scaffold and activation of the surface of the polymer scaffold by injecting the surface activating gas can be changed in order.

Cell compatibility of the porous polymer scaffold on which a hydrophilic monomer is grafted as described above can be evaluated with a cell adhesion test. Cells such as chondrocyte, cornea cell, skin cell, fibroblast, bone cell, liver cell, muscular cell, endothelial cell, smooth muscle cell, pancreas cell, nerve cell, etc. can be used for this test.

EXAMPLES

Hereinafter, the present invention will be described in more detail with reference to the following examples. However, the examples are to illustrate the present invention, and not to limit the scope of the present invention thereto.

Example 1

An effervescent mixture containing sodium carbonate and citric acid in a molar ratio of 3:1 and having a particle size of 200–300 μm was added to a 13 wt. % solution of poly-L-lactic acid having a molecular weight of 110,000 dissolved in dichloromethane such that the ratio of the effervescent mixture/PLLA is 20/1 by weight, and then the resulting mixture was mixed uniformly. The above mixture was poured into a frame made of a silicone material having a desired shape, and frozen by putting the frame into liquid nitrogen at −196° C. and leaving 2–3 minutes therein. The solvent was then evaporated with a freeze dryer for 24 hours, to obtain a polymer sample in a disc shape. The polymer sample in a disc shape was put into a solvent mixture of water and ethanol in a ratio of 50:50 by weight. A foaming process was carried out for 24 hours, and the polymer sample was then taken out to be freeze-dried. The obtained porous polymer scaffold shows 98% of porosity by being measured with a mercury intrusion porosimetry.

The obtained porous scaffold was then fixed between radio frequency generating electrodes located in a chamber of a plasma discharging apparatus, all valves of the apparatus were closed, and the pressure was then set up to be $10^{-3}$ torr with a vacuum pump. Under these conditions, acrylic acid was injected into the chamber in a gas phase. A monomer injecting valve was adjusted such that the pressure was 0.2 torr. When the desired pressure was maintained, the RF power and the pulse type negative voltage were applied in order to generate plasma. The RF power was 50 watt, and the discharging was performed for 30 seconds.

After the hydrophilic monomer was graft-polymerized on the surface of the porous polymer scaffold, the surface of the scaffold was activated by plasma discharging oxygen gas with the same RF power under the same pressure for the same time as described above, and then stabilized in air.

The hydrophilicity of the porous polymer scaffold surface which was modified as described above can be identified with a water contact angle. Water contact angles of the porous polymer scaffold fabricated in Examples are shown in Table 2. The initial water contact angle before the surface was modified was about 75°. However, the water contact angle after the surface was modified was about 35°. Accordingly, it was discovered that the hydrophilization was made effectively.

As shown in table 1, the hydrophilicity can be also identified with an oxygen atom content increase in an X-ray photoelectron spectroscopy (XPS) of the surface of the polymer scaffold made of poly-L-lactic acid.

TABLE 1

|  | Element content | | Ratio of carbon/ |
| --- | --- | --- | --- |
|  | Carbon | Oxygen | oxygen |
| Before treatment | 62.1 | 37.9 | 0.61 |
| After plasma treatment | 57.9 | 42.1 | 0.73 |

Before the plasma treatment, water did not infiltrate into the scaffold at all. However, after the plasma treatment, the water infiltrated into the scaffold effectively. As a result of calculating the number of cell adhered through a cartilage cell culture in vitro, it is discovered that the cell compatibility of the surface-modified polymer scaffold was improved than that of the polymer scaffold of which the surface was not modified. FIG. 1 is a photograph of scanning electron microscopy showing cell growth in the polymer scaffold made of poly-L-lactic acid. And it could be identified that the cells were distributed uniformly inside the polymer scaffold which was treated with a plasma.

Example 2

A porous polymer scaffold was fabricated in the same method as described in Example 1, except that 13 wt. % solution of poly(lactic acid-glycolic acid) copolymer having a molecular weight of 110,000 containing lactic acid and glycolic acid in a ratio of 50:50 by weight dissolved in chloroform, and porous effervescent mixture containing sodium bicarbonate and citric acid in a molar ratio of 3:1 and having a particle size of 200–300 $\mu$m were used. Surface of the obtained porous polymer scaffold was modified in the same way as described in Example 1 by plasma treatment, except that the acrylamide was used.

The obtained porous polymer scaffold showed similar hydrophilicity and improved cell compatibility to those of the porous polymer scaffold fabricated in Example 1.

Example 3

A porous polymer scaffold was fabricated in the same method as in Example 1, except that 13 wt. % solution of PLGA copolymer having a molecular weight of 140,000 containing lactic acid and glycolic acid in a ratio of 85:15 by weight dissolved in dichloromethane, and a porous effervescent mixture containing sodium bicarbonate and citiric acid in a molar ratio of 3:1 and having a particle size of 50–100 $\mu$m were used. Surface of the obtained porous polymer scaffold was modified in the same way as in Example 1 by plasma treatment, except that the acrylic acid and argon gas were used.

The surface-modified porous polymer scaffold showed similar hydrophilicity and improved cell compatibility to those of the porous polymer scaffold fabricated in Example 1.

Example 4

A porous polymer scaffold was fabricated in the same method as in Example 1, except that 10 wt. % solution of poly-DL-lactic acid having a molecular weight of 200,000 dissolved in dichloromethane and a porous effervescent mixture containing sodium bicarbonate and citric acid in a molar ratio of 3:1 and having a particle size of 100–200 $\mu$m were used. Surface of the obtained polymer scaffold was modified in the same way as in Example 1 by plasma treatment, except that the acrylamide and argon gas were used.

The surface-modified porous polymer scaffold showed similar hydrophilicity and improved cell compatibility to those of the porous polymer scaffold fabricated in Example 1.

Example 5

A porous polymer scaffold was fabricated in the same method as in Example 1, except that 13 wt. % solution of poly-$\epsilon$-caprolactone having a molecular weight of 100,000 dissolved in chloroform was used. Surface of the obtained porous polymer scaffold was modified by low temperature plasma treatment in the same way as in Example 1, except that hydroxyethyl methacrylate and nitrogen gas were used.

The surface-modified porous polymer scaffold showed similar hydrophilicity and improved cell compatibility to those of the porous polymer scaffold fabricated in Example 1.

Example 6

A porous polymer scaffold was fabricated in the same method as in Example 1, except that 13 wt. % solution of PLGA copolymer having a molecular weight of 110,000 containing lactic acid and citric acid in a ratio of 75:25 by weight dissolved in chloroform, and a porous effervescent mixture containing sodium bicarbonate and citric acid in a molar ratio of 3:1 and having a particle size of 100–200 $\mu$m were used. Surface of the obtained porous polymer scaffold was modified in the same way as in Example 1 by plasma treatment, except that hydroxyethyl methacrylate and carbon monoxide gas were used.

The surface-modified porous polymer scaffold showed similar hydrophilicity and improved cell compatibility to those of the porous polymer scaffold fabricated in Example 1.

Example 7

A porous polymer scaffold was fabricated in the same method as in Example 1, except that 10 wt. % solution of poly(glycolicacid-caprolactone) copolymer having a molecular weight of 200,000 containing glycolic acid and caprolactone in a ratio of 75:25 by weight dissolved in chloroform was used. Surface of the obtained porous polymer scaffold was modified in the same way as in Example 1 by low temperature plasma treatment, except that the allyl alcohol and carbon monoxide gas were used.

The surface-modified porous polymer scaffold showed similar hydrophilicity and improved cell compatibility to those of the porous polymer scaffold fabricated in Example 1.

Example 8

A porous polymer scaffold was fabricated in the same method as in Example 1, except that 15 wt. % solution of poly(SA-HDA anhydride) [1:1 copolymer of sebacic acid (SA) and hexadecandioic acid (HDA)] having a molecular weight of 80,000 dissolved in chloroform was used. Surface of the obtained porous polymer scaffold was modified in the same way as in Example 1 by plasma treatment, except that polyethylene glycol monoacrylate having a molecular weight of about 200 and carbon dioxide gas were used.

The surface-modified porous polymer scaffold showed similar hydrophilicity and improved cell compatibility to those of the porous polymer scaffold fabricated in Example 1.

Example 9

A porous polymer scaffold was fabricated in the same method as in Example 1, except that 13 wt. % solution of PLGA copolymer having a molecular weight of 100,000 containing lactic acid and glycolic acid in a ratio of 90:10 by weight dissolved in chloroform was used. Surface of the obtained porous polymer scaffold was modified in the same way as in Example 1 by plasma treatment, except that polyethylene glycol monomethacrylate having a molecular weight of 2,000 and carbon dioxide gas were used.

The surface-modified porous polymer scaffold showed similar hydrophilicity and improved cell compatibility to those of the porous polymer scaffold fabricated in Example 1.

Example 10

A porous polymer scaffold was fabricated in the same method as in Example 1, except that 13 wt. % solution of poly(DETOSU-1,6HD-t-CDM orthoester) {100:35:64 copolymer of 3,9-bis(ethylidene 2,4,8,10-tetaoxaspiro [5,5] undecane) (DETOSU), 1,6-hexanediol (1,6-DH), and trans-cyclohexane dimethanol (t-CDM)} having a molecular weight of 10,000 dissolved in chloroform was used. Surface of the obtained porous polymer scaffold was modified in the same way as in Example 1 by plasma treatment, except that glycidyl methacrylate and ammonia gas were used.

The surface-modified porous polymer scaffold showed similar hydrophilicity and improved cell compatibility to those of the porous polymer scaffold fabricated in Example 1.

Example 11

A porous polymer scaffold was fabricated in the same method as in Example 1, except that 10 wt. % solution of poly-D-lactic acid having a molecular weight of 700,000 dissolved in chloroform was used. Surface of the obtained porous polymer scaffold was modified in the same way as in Example 1 by plasma treatment, except that aminopropyl methacrylamide and ammonia gas were used.

The surface-modified porous polymer scaffold showed similar hydrophilicity and improved cell compatibility to those of the porous polymer scaffold fabricated in Example 1.

The following Table 2 shows water contact angles before and after surface modification of the polymer scaffolds fabricated in Examples 1 though 11. From the results of the water contact angles, it can be discovered that the hydrophilicity of the polymer scaffold surface was improved effectively.

TABLE 2

| Example Nos. | Monomer graft-polymerized | Discharge gas | Water contact angles (°) | |
|---|---|---|---|---|
| | | | Before treatment | After treatment |
| Example 1 | Acrylic acid | Oxygen | 75 | 35 |
| Example 2 | Acrylamide | Oxygen | 78 | 40 |
| Example 3 | Acrylic acid | Argon | 78 | 37 |
| Example 4 | Acrylamide | Argon | 75 | 39 |
| Example 5 | Hydroxyethyl methacrylate | Nitrogen | 73 | 34 |
| Example 6 | Hydroxyethyl methacrylate | Carbon monoxide | 78 | 34 |
| Example 7 | Allyl alcohol | Carbon monoxide | 75 | 42 |
| Example 8 | Polyethylene glycol monoacrylate | Carbon dioxide | 79 | 28 |
| Example 9 | Polyethylene glycol monomethacrylate | Carbon dioxide | 78 | 29 |
| Example 10 | Glycidyl methacrylate | Ammonia | 80 | 43 |
| Example 11 | Aminopropyl methacrylamide | Ammonia | 75 | 37 |

As described above, the present invention provides a fabrication method of a biodegradable porous polymer scaffold for tissue engineering having an improved cell compatibility through modifying a hydrophobic surface of the porous polymer scaffold into hydrophilic. Therefore, it can be solved the problems of conventional art such as lack of a cell and tissue compatibility, lowering of mechanical property and immune reaction according to the use of an extracellular matrix of different species according to the present invention. In addition, in the fabrication method of the present invention, the surface treatment time is very short and a lot of chemicals are not needed. Accordingly, the biodegradable porous polymer scaffold of the present invention can be applied widely in the fields such as reconstruction and regeneration of artificial tissue and organs by tissue engineering technique.

As the present invention may be embodied in several forms without departing from the spirit or essential characteristics thereof, it should also be understood that the above-described Examples are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. A method for preparing a biodegradable porous polymer scaffold having an improved cell compatibility for tissue engineering comprising a surface modification of a biodegradable porous polymer scaffold, by treating surface of the biodegradable porous polymer scaffold with a low temperature plasma and an unsaturated aliphatic hydrocarbon monomer having a hydrophilic group.

2. The method according to claim 1, wherein the surface modification comprises:

(a) graft-polymerizing an unsaturated aliphatic hydrocarbon monomer having a hydrophilic group on the surface of the biodegradable porous polymer scaffold;

(b) activating the surface of the biodegradable porous polymer scaffold obtained in step (a) with a surface activating gas; and (c) stabilizing the biodegradable porous polymer scaffold obtained in step (b) in air.

3. The method according to claim 2, wherein the graft-polymerization in step (a) comprises:

inserting a biodegradable porous polymer scaffold into a chamber of a low temperature plasma discharge apparatus, and then maintaining the chamber in a vacuum;

injecting an unsaturated aliphatic hydrocarbon monomer having a hydrophilic group into the chamber in a gas phase; and plasma discharging with a radio frequency power, thereby to perform a graft-polymerization of the unsaturated aliphatic hydrocarbon monomer on the surface of the biodegradable porous polymer scaffold.

4. The method according to claim 3, wherein the aliphatic hydrocarbon monomer is injected at a pressure of $5 \times 10^{-2}$–$3 \times 10^{-1}$ torr.

5. The method according to claim 3, wherein the plasma discharge is performed with a radio frequency power of 50–1,000 W for 10–300 seconds.

6. The method according to claim 2, wherein the activation in step (b) comprises:

injecting a surface activating gas into the chamber; and plasma discharging with a radio frequency power, thereby to activate the surface of the porous polymer scaffold obtained in step (a).

7. The method according to claim 6, wherein the activating gas is injected at a pressure of $5 \times 10^{-2}$–$3 \times 10^{-1}$ torr.

8. The method according to claim 6, wherein the plasma discharge is performed with a radio frequency power of 50–1,000 W for 10–300 seconds.

9. The method according to claim 2, wherein the surface activating gas is selected from the group consisting of oxygen, nitrogen, argon, carbon monoxide, carbon dioxide, ammonia and mixtures thereof.

10. The method according to claim 1, wherein the biodegradable polymer is selected from the group consisting of polyglycolic acid, poly-L-lactic acid, poly-DL-lactic acid, poly-D-lactic acid, poly(lactic acid-glycolic acid) copolymer, poly-$\epsilon$-caprolactone, poly(glycolic acid-caprolactone) copolymer, polyamino acid, polyanhydride, polyorthoester, and copolymers and mixtures thereof.

11. The method according to claim 1, wherein the unsaturated aliphatic hydrocarbon monomer having a hydrophilic group is selected from the group consisting of acrylic acid, acrylamide, hydroxyethyl methacrylate, allyl alcohol, polyethylene glycol monoacrylate, polyethylene glycol monomethacrylate, glycidyl methacrylate, aminopropyl methacrylamide and mixtures thereof.

12. The method according to claim 11, wherein molecular weights of the polyethylene glycol monoacrylate and polyethylene glycol monomethacrylate are 200–2000, respectively.

* * * * *